United States Patent
Rosen et al.

(10) Patent No.: US 11,504,226 B2
(45) Date of Patent: Nov. 22, 2022

(54) INTRAOCULAR LENSES FOR REDUCING THE RISK OF POSTERIOR CAPSULE OPACIFICATION

(71) Applicant: AMO Groningen B.V., Groningen (NL)

(72) Inventors: Robert Rosen, Groningen (NL); Hendrik A. Weeber, Groningen (NL); Carmen Canovas Vidal, Groningen (NL); Robin Zonneveld, Groningen (NL); Sieger Meijer, Groningen (NL); Bram Koopman, Groningen (NL); Bart Cannegieter, Groningen (NL); Theophilus Bogaert, Groningen (NL); Aixa Alarcon Heredia, Groningen (NL); Mihai State, Groningen (NL)

(73) Assignee: AMO Groningen B.V., Groningen (NL)

(*) Notice: Subject to any disclaimer, the term of this patent is extended or adjusted under 35 U.S.C. 154(b) by 0 days.

(21) Appl. No.: 17/057,096

(22) PCT Filed: Oct. 21, 2019

(86) PCT No.: PCT/EP2019/078554
§ 371 (c)(1),
(2) Date: Nov. 19, 2020

(87) PCT Pub. No.: WO2020/083828
PCT Pub. Date: Apr. 30, 2020

(65) Prior Publication Data
US 2021/0236268 A1    Aug. 5, 2021

Related U.S. Application Data

(60) Provisional application No. 62/750,148, filed on Oct. 24, 2018.

(51) Int. Cl.
*A61F 2/16*    (2006.01)

(52) U.S. Cl.
CPC .... *A61F 2/1613* (2013.01); *A61F 2002/1681* (2013.01)

(58) Field of Classification Search
CPC ...... A61F 2/16; A61F 2/1601; A61F 2/16015; A61F 2/1613; A61F 2002/1681
See application file for complete search history.

(56) References Cited

U.S. PATENT DOCUMENTS

| 4,676,791 A | 6/1987 | LeMaster et al. |
| 5,480,950 A | 1/1996 | Wang et al. |

(Continued)

FOREIGN PATENT DOCUMENTS

| WO | 03077803 A1 | 9/2003 |
| WO | 2006054130 A1 | 5/2006 |

(Continued)

OTHER PUBLICATIONS

Curcio C, C., et al., "Human Photoreceptor Topography," The Journal of Comparative Neurology, 1990, vol. 292, pp. 497-523.

(Continued)

*Primary Examiner* — William H Matthews
(74) *Attorney, Agent, or Firm* — Johnson & Johnson Surgical Vision, Inc.

(57) ABSTRACT

Intraocular lenses for reducing the risk of posterior capsule opacification (PCO) are described herein. PCO can be reduced with an IOL design that increases the pressure at the posterior capsular bend, for example, by including a sharper edge design, an enlarged optical zone, and/or an increased vault height. An example ophthalmic lens can include an optic (200) including an anterior surface (202) defining an anterior side of the optic, a posterior surface (204) defining a posterior side of the optic, and an edge (210) arranged between the anterior and posterior surfaces. The edge and the posterior surface can form an angle, where the angle is (Continued)

less than about 90 degrees. Additionally, the ophthalmic lens can have an increased vault height. At least one of the angle or the increased vault height be configured to increase pressure on a capsular bend in a subject's eye.

11 Claims, 14 Drawing Sheets

(56) References Cited

U.S. PATENT DOCUMENTS

| | | | |
|---|---|---|---|
| 5,578,081 | A | 11/1996 | McDonald |
| 5,702,441 | A | 12/1997 | Zhou |
| 5,755,786 | A | 5/1998 | Woffinden et al. |
| 6,468,306 | B1 | 10/2002 | Paul et al. |
| 6,533,814 | B1 * | 3/2003 | Jansen .................. A61F 2/1613 623/6.43 |
| 8,696,746 | B2 | 4/2014 | Wanders et al. |
| 10,588,738 | B2 | 3/2020 | Rosen et al. |
| 2003/0114926 | A1 | 6/2003 | Paul et al. |
| 2003/0130733 | A1 | 7/2003 | Paul et al. |
| 2003/0144733 | A1 | 7/2003 | Brady et al. |
| 2005/0041203 | A1 | 2/2005 | Lindacher et al. |
| 2005/0060031 | A1 | 3/2005 | Coroneo et al. |
| 2005/0246016 | A1 | 11/2005 | Miller et al. |
| 2007/0239274 | A1 * | 10/2007 | Kellan .................. A61F 2/1629 623/6.44 |
| 2007/0244560 | A1 | 10/2007 | Ossipov et al. |
| 2008/0077239 | A1 | 3/2008 | Zickler et al. |
| 2008/0269882 | A1 | 10/2008 | Simpson et al. |
| 2008/0269885 | A1 | 10/2008 | Simpson et al. |
| 2008/0269886 | A1 | 10/2008 | Simpson et al. |
| 2008/0269890 | A1 | 10/2008 | Simpson et al. |
| 2009/0018651 | A1 | 1/2009 | Zhang et al. |
| 2009/0033863 | A1 | 2/2009 | Blum et al. |
| 2014/0180408 | A1 | 6/2014 | Angelopoulos et al. |

FOREIGN PATENT DOCUMENTS

| | | |
|---|---|---|
| WO | 2010100523 A1 | 9/2010 |
| WO | 2019126649 A1 | 6/2019 |

OTHER PUBLICATIONS

Curcio C.A., et al., "Topography of Ganglion Cells in Human Retina," The Journal of Comparative Neurology, 1990, vol. 300, pp. 5-25.

Holladay J.T., et al., "Negative Dysphotopsia: The Enigmatic Penumbra," Journal Cataract and Refractive Surgery, Jan. 2012, vol. 38 (7), pp. 1251-1265.

Hong X., et al., "Ray-Tracing Optical Modeling of Negative Dysphotopsia," Journal of Biomedical Optics, Dec. 2011, vol. 16 (12), p. 125001.

Spector R.H., "Chapter 116 Visual Fields Figure 116.1" Clinical Methods: The History, Physical, and Laboratory Examinations, 3rd Edition Walker HK, Hall WD, Hurst JW 1990, Retrieved from the Internet: (https://www.ncbi.nlm.nih.gov/books/NBK220/), 8 Pages.

* cited by examiner ns
INTRAOCULAR LENSES FOR REDUCING THE RISK OF POSTERIOR CAPSULE OPACIFICATION

CROSS REFERENCES TO RELATED APPLICATIONS

This application is a U.S. national stage of and claims the benefit under 35 U.S.C. § 371 of International Patent Application No. PCT/EP2019/078554, filed Oct. 21, 2019, which claims the benefit under 35 U.S.C. § 119(e) of U.S. Provisional Patent Application No. 62/750,148 filed Oct. 24, 2018, which are incorporated herein by reference in their entirety.

BACKGROUND

Posterior capsule opacification (PCO) results from lens fibers formed in the equatorial zone that migrate over the posterior side of an IOL, which can result in reduced visual quality and potentially requires a secondary intervention with an NdYAG laser. While results vary, and improved IOL designs have substantially reduced the rate of PCO the last few decades, it is still a significant issue negatively affecting the results of cataract surgery. The current state of the art for PCO prevention is a PCO edge covering the full IOL (360 degrees) with an angle of around 90-110 degrees, including on the haptics.

Negative dysphotopsia (ND) is characterized by subjective reports and complaints from patients having an intraocular lens (IOL) implanted, where the complaints describe the presence of a dark shadow in the far periphery. A number of patient factors, including small photopic pupil, high angle kappa and hyperopia, have been identified as increasing the risk of ND. The presence of ND is likely caused by absence of light in the retinal interval between light passing through and refracted by the IOL (e.g., at lower angles of incidence) and rays missing the IOL (e.g., at higher angles of incidence). While the light passing the IOL at the lower angles of incidence is refracted, changing its direction to a lower angle, the light at the higher angles miss the IOL and continue straight without deviation, thereby creating an angular interval on the retina that is not illuminated. The problem is partially alleviated at larger pupil sizes, since optical errors create larger deviations of rays at the pupil edge which partially hits the obscured part of the peripheral retina. On the other hand, for smaller pupils the pinhole effect exacerbates the ND effect. For the natural crystalline lens, ND is not a problem, since no light will miss the lens as it is larger and closer to the pupil. Currently, there are no IOLs on the market designed to prevent ND.

SUMMARY

Intraocular lenses for reducing the risk of posterior capsule opacification (PCO) are described herein. PCO can be reduced with an IOL design that increases the pressure at the posterior capsular bend, for example, by including a sharper edge design, an enlarged optical zone, and/or an increased vault height. An example ophthalmic lens can include an optic including an anterior surface defining an anterior side of the optic, a posterior surface defining a posterior side of the optic, and an edge arranged between the anterior and posterior surfaces. The edge and the posterior surface can form an angle, where the angle is less than about 90 degrees. Additionally, the ophthalmic lens can have an increased vault height. At least one of the angle or the increased vault height can be configured to increase pressure on a capsular bend in a subject's eye.

In some implementations, a combination of the angle and the increased vault height can be configured to increase pressure on the capsular bend in the subject's eye.

Alternatively or additionally, the angle can be between about 45 degrees and about 90 degrees. Optionally, the angle can be less than about 85 degrees. Optionally, the angle can be less than about 80 degrees. Optionally, the angle can be less than about 70 degrees. Optionally, the angle can be less than about 60 degrees. Optionally, the angle can be less than about 50 degrees.

Alternatively or additionally, a diameter of the anterior side of the optic can be less than a diameter of the posterior side of the optic.

Alternatively or additionally, the increased vault height can be between about 0.35 millimeter (mm) and about 1.5 mm.

Alternatively or additionally, a diameter of the optic can be between about 6 mm and about 8 mm.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIGS. 12A-12C are plots where the angle is greater than 90 degrees, e.g., existing commercial IOL designs following a radius of curvature of 10 mm (FIG. 12A), 15 mm (FIG. 12B), 20 mm (FIG. 12C) at 6 mm diameter, which result in angles of 107 degrees, 102 degrees, and 99 degrees, respectively. FIG. 12D is a plot where the angle is 90 degrees. The IOL in FIG. 12D can be designed according to implementations described herein.

DETAILED DESCRIPTION

Figure 1A:
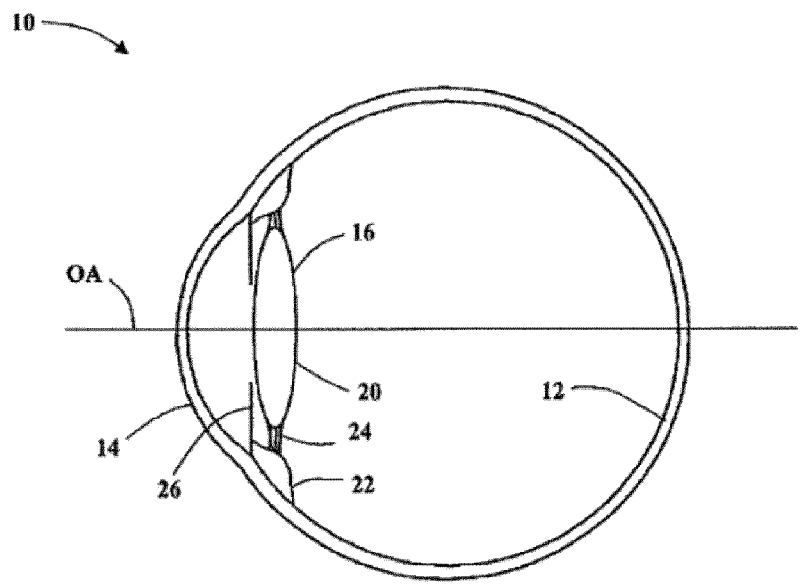
FIG. 1A illustrates a side view of an eye containing a natural crystalline lens.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. While implementations are described for intraocular lenses, it will become evident to those skilled in the art that the implementations are not limited thereto, but are applicable for other ophthalmic lenses.

Described herein is an IOL that substantially reduces negative dysphotopsia through changes of IOL design in the form of introducing an attenuation optical zone (also referred to herein as "attenuation zone"). While conventional IOLs on the market have an optical zone size of about 5 or 6 mm in diameter (and nothing outside the edge of that zone), the IOLs described herein increase the optical diameter by about 0.5-3 mm, bringing the total optical diameter of the IOL potentially up to 8 mm. The purpose of the attenuation zone is to act as a bridge between light at angles where the light is refracted by the IOL and where the light misses the IOL. The attenuation zone gradually decreases the deviation of light with higher angles, until light at angles just at the edge of the IOL are almost not refracted at all, making the difference to light at angles missing the IOL minimal.

An IOL that reduces or attenuates ND as described herein can include: a central optical zone for central vision and/or functional peripheral vision; and an attenuation optical zone that gradually reduces the power in the outer or peripheral part of the IOL. It should be understood that monofocal, multifocal, and Extended Depth of Focus (EDoF) IOLs are used for central vision. As used herein, functional peripheral vision is vision within less than about 40 degrees of the visual field. The attenuation zone does not contribute to either central vision or functional peripheral vision (e.g., vision below 40 degrees of the visual field) unless the pupil is exceptionally large. Optionally, as described herein, the IOL that reduces or attenuates ND can include a sharp IOL edge design.

The central optical zone of the IOL is independent of the attenuation optical zone. Accordingly, this disclosure contemplates that the attenuation zone and/or the sharp edge design described herein can be added to any IOL design because neither affects central vision or peripheral vision below 40 degrees. Accordingly, the attenuation zone and/or sharp edge design can be added to refractive and diffractive IOLs as well as to monofocal, multifocal and extended range of vision IOLs.

Also described herein is an IOL that increases pressure at the posterior capsular bend, which reduces the possibility of cell growth and migration onto the optics of the IOL. Such cell growth and migration reduces the structure disposed about the peripheral region of the optic, which results in the presence of glare or posterior capsular opacification (PCO). An IOL that reduces the risk of PCO can include one or more of the following: a sharper edge design, an enlarged optical zone, and/or an increased vault height.

As used herein, the terms "about" or "approximately", when used in reference to an angle (e.g., angle θ in FIG. 2B), mean within plus or minus 1 degree. As used herein, the terms "about" or "approximately", when used in reference to a linear dimension (e.g., length, width, thickness, distance, radius, diameter, etc.) mean within plus or minus 5% of the value of the referenced linear dimension.

As used herein, the terms "light" or "visible light" mean electromagnetic radiation within the visible waveband, for example, electromagnetic radiation with a wavelength in a vacuum that is between 390 nanometers and 780 nanometers. As used herein, the term "optical power" of a lens or optic means the ability of the lens or optic to converge or diverge light to provide a focus (real or virtual) when disposed within a media having a refractive index of 1.336 (generally considered to be the refractive index of the aqueous and vitreous humors of the human eye), and is specified in reciprocal meters or Diopters (D). See ISO 11979-2. As used herein the terms "focus" or "focal length" of a lens or optic is the reciprocal of the optical power. As used herein the term "power" of a lens or optic means optical power. Except where noted otherwise, optical power (either absolute or add power) of an intraocular lens or associated optic is from a reference plane associated with the lens or optic (e.g., a principal plane of an optic).

As used herein, the term "near vision" means vision produced by an eye that allows a subject to focus on objects that are at a distance of 40 cm or closer to a subject, typically within a range of 25 cm to 33 cm from the subject, which corresponds to a distance at which a subject would generally place printed material for the purpose of reading. As used herein, the term "intermediate vision" means vision produced by an eye that allows a subject to focus on objects that are located between 40 cm and 2 meters from the subject. As used herein, the term "distant vision" means vision produced by an eye that allows a subject to focus on objects that are at a distance that is greater than 2 meters, typically at a distance of about 5 meters from the subject, or at a distance of about 6 meters from the subject, or greater.

Referring now to FIG. 1A, a cross-sectional view of a phakic eye containing the natural crystalline lens is shown in which an eye 10 includes a retina 12 that receives light in the form of an image produced when light from an object is focused by the combination of the optical powers of a cornea 14 and a natural crystalline lens 16. The cornea 14 and lens 16 are generally disposed about an optical axis (OA). As a general convention, an anterior side is considered to be a side closer to the cornea 14, while a posterior side is considered to be a side closer to the retina 12.

The natural lens 16 is enclosed within a capsular bag 20, which is a thin membrane attached to a ciliary muscle 22 via zonules 24. An iris 26, disposed between the cornea 14 and the natural lens 16, provides a variable pupil that dilates under lower lighting conditions (mesopic or scotopic vision) and constricts under brighter lighting conditions (photopic vision). The ciliary muscle 22, via the zonules 24, controls the shape and position of the natural lens 16, allowing the eye 10 to focus on both distant and near objects. It is generally understood that distant vision is provided when the ciliary muscle 22 is relaxed, wherein the zonules 24 pull the natural lens 16 so that the capsular bag 20 and lens 16 are generally flatter and provide a longer focal length (lower optical power). It is generally understood that near vision is provided when the ciliary muscle contracts, thereby relaxing the zonules 24 and allowing the capsular bag 20 and lens 16 to return to a more rounded state that produces a shorter focal length (higher optical power).

Figure 1B:
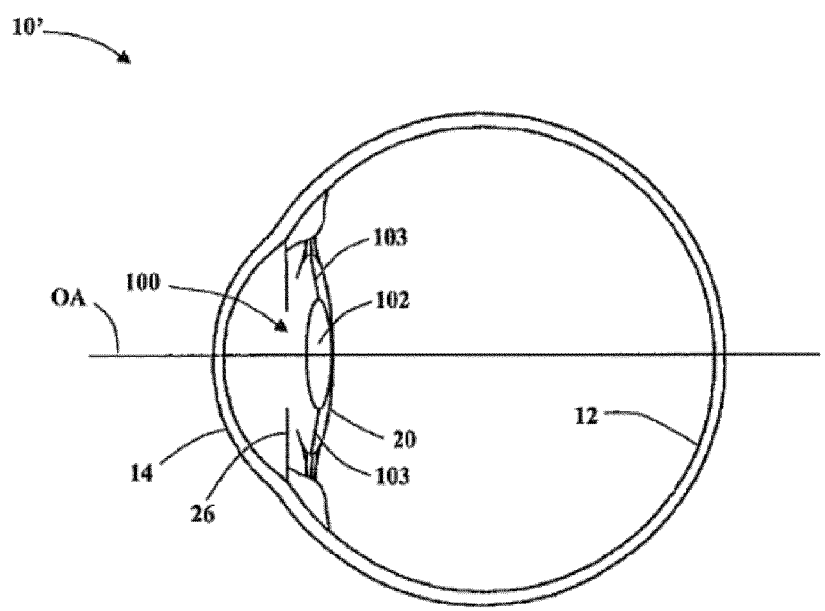
FIG. 1B illustrates a side view of the eye shown in FIG. 1A with an IOL according to an implementation described herein.

Referring now to FIG. 1B, a cross-sectional view of a pseudophakic eye is shown in which the natural crystalline lens 16 has been replaced by an intraocular lens 100 according to an implementation described herein. The intraocular lens 100 can include an optic 102 and haptics 103, the haptics 103 being configured to at least generally center the optic 102 within the capsular bag 20, provide transfer of ocular forces to the optic 102, and the like. Numerous configurations of haptics 103 relative to optic 102 are well known within the art, and the optics described herein can generally include any of these haptic configurations.

Figure 2A:
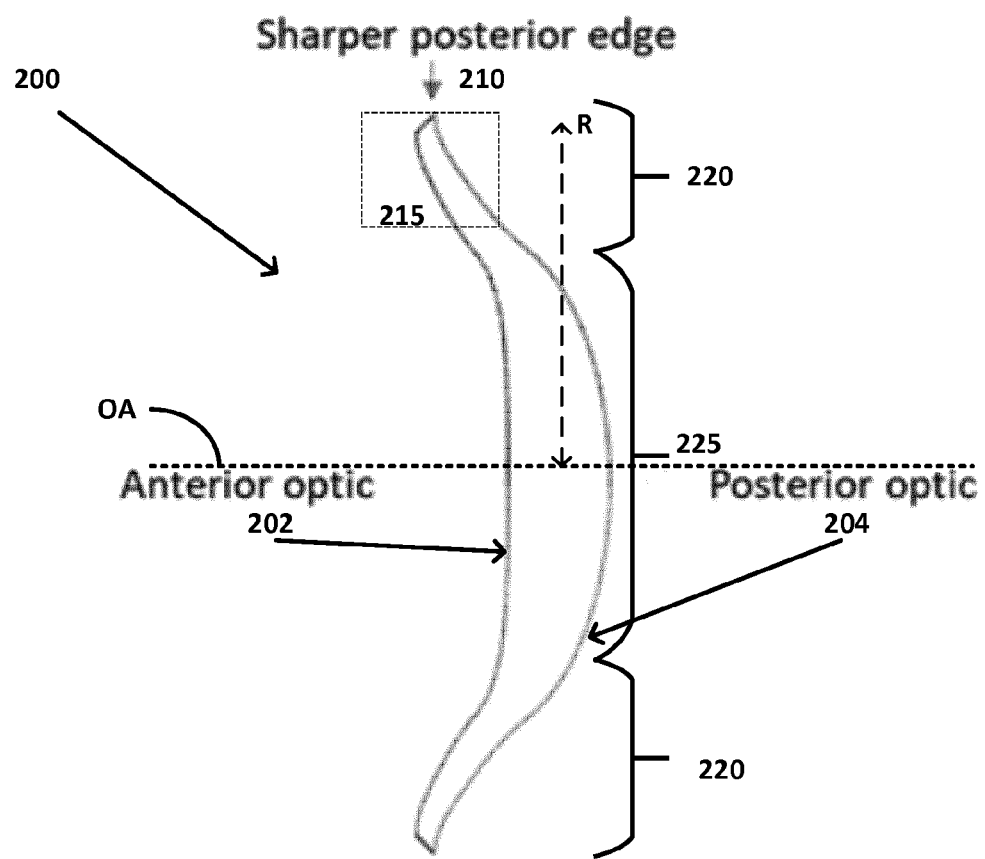
FIG. 2A is a cross-sectional view illustrating of the optic of an example IOL according to an implementation described herein. The optic shown in FIG. 2A can reduce rates of PCO and/or reduce ND.
Figure 2B:
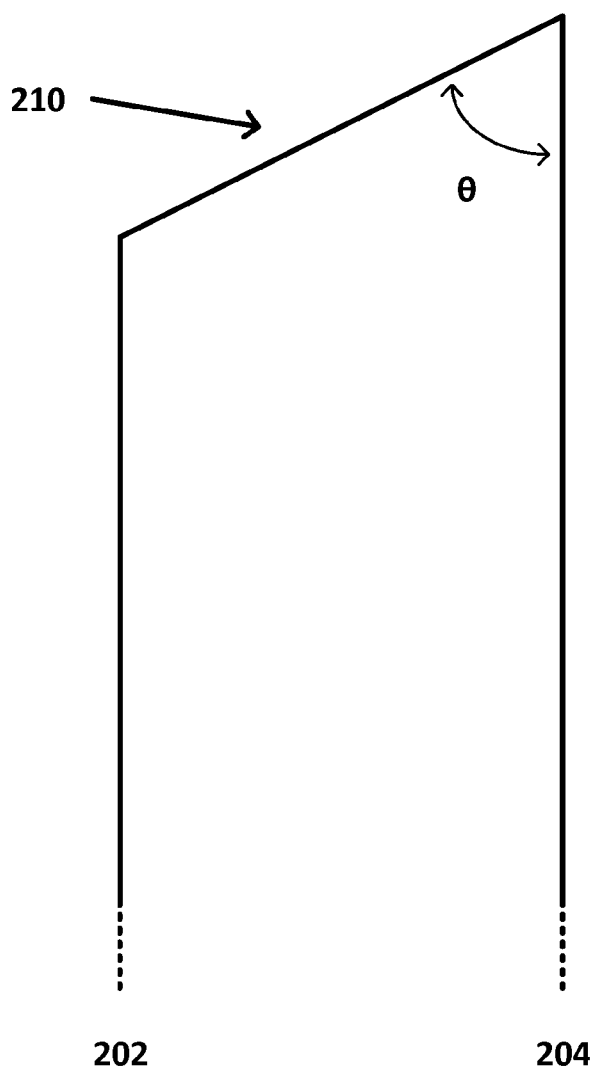
FIG. 2B is an exaggerated view illustrating the edge of the optic shown in FIG. 2A.
Figure 2C:
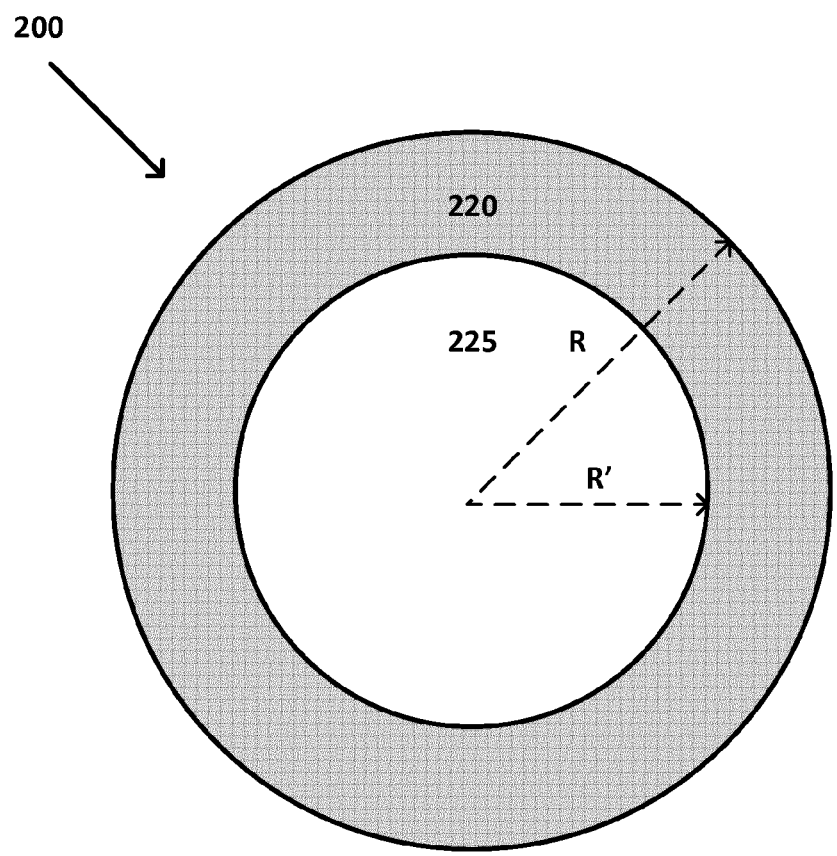
FIG. 2C is a view illustrating central and attenuation optical zones of the optic shown in FIG. 2A.

Referring now to FIGS. 2A-2C, an example ophthalmic lens is described. In the implementations described herein, the ophthalmic lens is an IOL. For example, the ophthalmic lens can be a refractive or diffractive IOL. Alternatively or additionally, the ophthalmic lens can be a monofocal, multifocal, or extended range of vision IOL. It should be understood that the IOL types described above are only provided as examples and that the ophthalmic lens can be an IOL other than one of the types provided as examples. The IOL described with regard to FIGS. 2A-2C can reduce the rate of PCO. Alternatively or additionally, the IOL described with regard to FIGS. 2A-2C can reduce ND.

The ophthalmic lens can include an optic 200 including an anterior surface 202 defining an anterior side of the optic 200 and a posterior surface 204 defining a posterior side of the optic 200. The posterior surface 204 can oppose the anterior surface 202. The optic 200 can also include an edge 210 arranged between the anterior and posterior surfaces 202, 204. The optical axis is labelled "OA" in FIG. 2A and extends through about the center of the optic 200.

Figure 3:
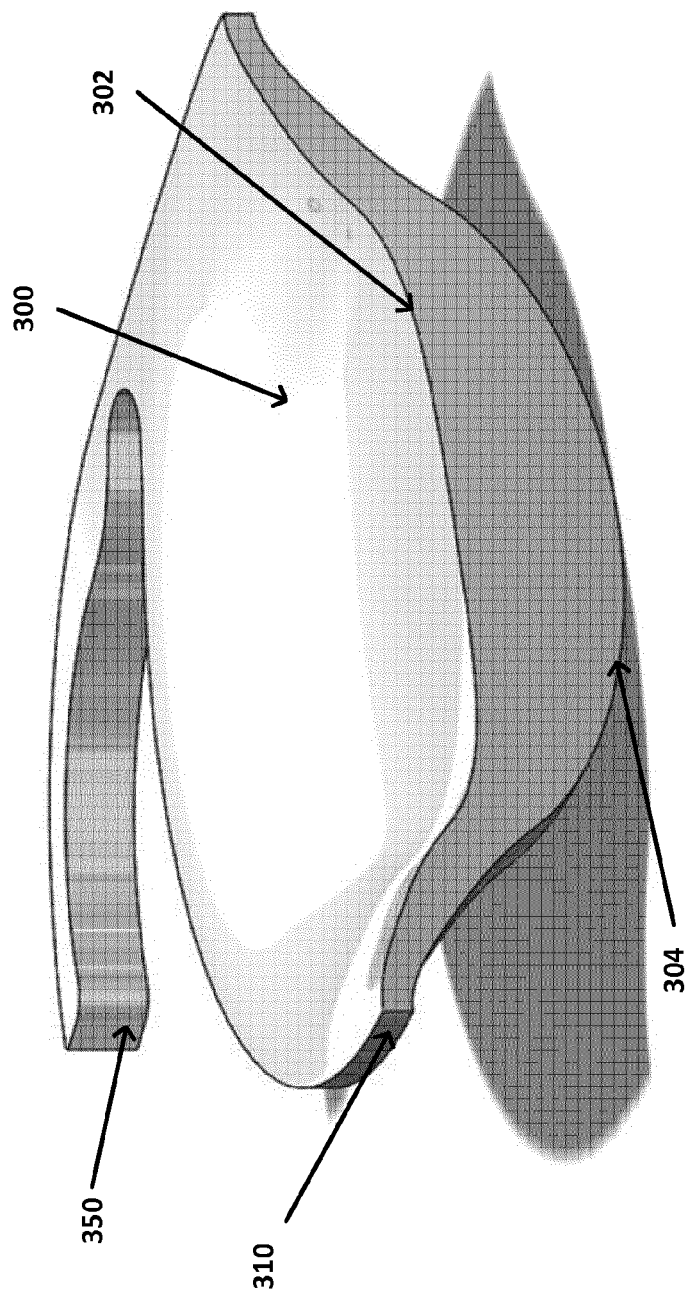
FIG. 3 is a perspective view (e.g., three-dimensional or 3-D view) of an example IOL having an enlarged optical zone and increased vault height according to an implementation described herein. The IOL shown in FIG. 3 can reduce rates of PCO and reduce ND.
Figure 12A:
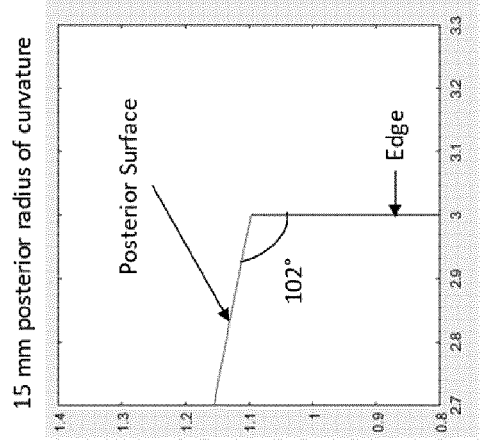
FIGS. 12A-12D are plots illustrating the angle formed between the posterior surface of the optic and the edge of various IOLs.
Figure 12B:
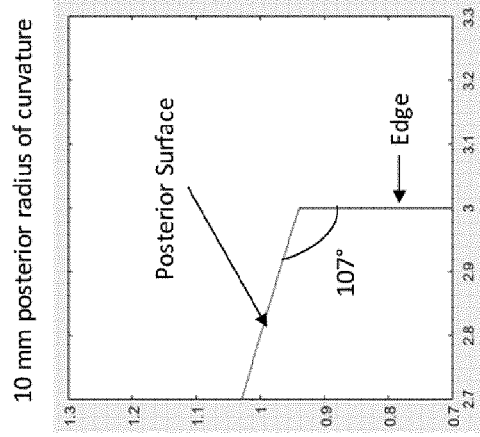
Figure 12C:
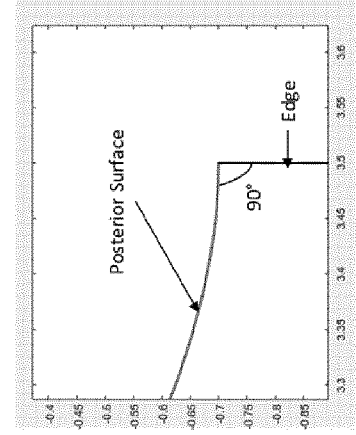
Figure 12D:
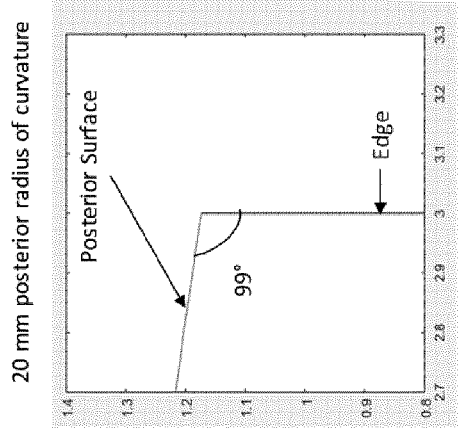

The rate of PCO can be reduced by including one or more of the following elements: a sharper edge design (e.g., the edge 210 shown in FIGS. 2A and 2B), an enlarged optical zone (e.g., including the attenuation optical zone 220 in addition to the central optical zone 225 shown in FIGS. 2A and 2C), and/or an increased vault height (e.g., as shown in FIGS. 2A and 3). Regarding edge design, existing commercial IOLs do not include the sharper edge designs described herein (e.g., less than about 90 degrees). For example, the edge of an IOL would have an angle of 107 degrees, 102 degrees, and 99 degrees, respectively, following a radius of curvature of 10 mm, 15 mm, and 20 mm, respectively, at 6 mm optic diameter. This is shown by FIGS. 12A-12C. These angles are greater than 90, and bad for PCO. An IOL with an edge angle of 90 degrees is shown in FIG. 12D for comparison. Alternatively or additionally, ND can be reduced by including one or more of the following elements: an enlarged optical zone (e.g., including the attenuation optical zone 220 in addition to the central optical zone 225 shown in FIGS. 2A and 2C) and/or a sharper edge design (e.g., the edge 210 shown in FIGS. 2A and 2B). ND can be eliminated using a sharp edge design with an angle of about 90 degrees. Using an angle of about 90 degrees may reduce manufacturing challenges depending on the technique used for producing the IOL. Alternatively, ND can be eliminated using a sharp edge design with an angle of less than 90 degrees.

The IOLs described herein can include a sharper edge design as compared to conventional IOLs. This disclosure contemplates that the sharper edge can be provided along the entire edge—360 degrees—of the optic. For example, as shown in FIG. 2B, the edge 210 and the posterior surface 204 can form an angle (e.g., angle θ). The edge with angle θ can be configured to increase pressure on a capsular bend in a subject's eye. For example, angle θ can be 90 degrees. In this implementation, the edge 210 is parallel to the optical axis of the ophthalmic lens. An IOL with angle θ equal to about 90 degrees can decrease or even eliminate ND and reduce PCO. Optionally, angle θ can be less than 90 degrees such as between 45 degrees and 90 degrees. In this implementation, the edge 210 is not parallel to the optical axis of the ophthalmic lens. For comparison, in existing commercial IOLs, the edge of an IOL is cut such that the angle formed between the edge and posterior surface is greater than 90 degrees but less than 110 degrees. Examples where the edge of an existing IOL would have an angle between 99 and 107 degrees are discussed above with regard to FIGS. 12A-12C. FIG. 2B is an enlarged view of the portion of the optic 200 in the dashed box 215, which includes the edge 210, shown in FIG. 2A. FIG. 2B illustrates angle θ. As described herein, the angle θ can be between 45 degrees and 90 degrees. In some implementations, the angle θ can be less than or equal to about 90 degrees. In some implementations, the angle θ can be less than about 90 degrees. In some implementations, the angle θ can be less than or equal to about 85 degrees. In some implementations, the angle θ can be less than or equal to about 80 degrees. In some implementations, the angle θ can be less than or equal to about 70 degrees. In some implementations, the angle θ can be less than or equal to about 60 degrees. In some implementations, the angle θ can be less than or equal to about 50 degrees. Having an angle θ as described above (e.g., a sharper edge design) results in a higher pressure at the capsular bend, which lowers risk of PCO. Alternatively or additionally, the angle θ as described above (e.g., a sharper edge design) reduces ND. Such a sharp angle of the edge 210 can be achieved by enlarging the optical zone size (as described below) and/or having an anterior side with an equal or smaller diameter as compared to a posterior side. For example, the diameter of the anterior surface 202 that forms the anterior side is less than the diameter of the posterior surface 204 that forms the posterior side as shown in FIG. 2A, which results in a sharp edge angle of less than 90 degrees. For designs where the sharp angle of edge 210 is 90 degrees, the diameter of the anterior surface 202 that forms the anterior side would be equal to the diameter of the posterior surface 204 that forms the posterior side.

The IOLs described herein can include an enlarged optical zone as compared to conventional IOLs. For example, the ophthalmic lens can include a central optical zone 225 disposed about the optical axis and an attenuation optical zone 220 disposed about the central optical zone 225. These zones are shown in FIGS. 2A and 2C. The central optical zone 225 and the attenuation optical zone 220 are defined by respective shapes of the anterior and posterior surfaces 202, 204 of the optic 200. For example, the shapes or contours of the anterior and posterior surfaces 202, 204 control the design parameters (e.g., height, thickness, width, curvature, etc.) of the optic 200. The central optical zone 225 extends radially outward from about the center of the optic (e.g., where the optical axis intersects the optic 200 as shown in FIG. 2A) to the radius (R') as shown in FIG. 2C. The central optical zone 225 is configured for central vision and/or functional peripheral vision, e.g., the central optical zone 225 is optimized for central vision and/or functional peripheral vision, which is below 40 degrees of the visual field. In some implementations, the central optical zone 225 has a diameter of about 5-6 mm).

The IOLs described herein can include the attenuation optical zone 220, which is in addition to the central optical zone 225. Having an attenuation zone as described herein results in a higher pressure at the capsular bend, which lowers risk of PCO. Alternatively or additionally, the attenuation zone reduces ND. The attenuation optical zone also facilitates the provision of a sharper edge design as described above. The attenuation optical zone 220 is contiguous with the central optical zone 225. The central optical zone 225 and the attenuation optical zone 220 can optionally be concentric. Unlike the central optical zone 225, however, the attenuation optical zone 220 is configured to not affect central vision and/or peripheral vision below 40 degrees Additionally, the transition between the central optical zone 225 and attenuation optical zone 220 can be smooth and continuous. The optic 200 can be configured such that the start (or beginning) of the optical attenuation zone 220 (e.g., the nearest attenuation region radially outward from the center of the optic) has the same coordinate and the same slope as the end of the central optical zone 225 (e.g., the most distant central region radially outward from the center of the optic 200). Design of the optic is described in further detail below with regard to FIGS. 4-11. Therefore, the central and attenuation optical zones connect seamlessly. The attenuation optical zone 220 extends radially outward from about the central optical zone 225 from radius (R') to radius (R) as shown in FIG. 2C. As described herein, optical power can be gradually reduced within the attenuation optical zone 220. For example, optical power of the ophthalmic lens can optionally be gradually reduced to zero at an outermost edge of attenuation optical zone 220 (e.g., at edge 210 as shown in FIGS. 2A and 2B). Gradual reduction in optical power is now described with reference to FIGS. 5 and 7. Normally, as the angle of the chief rays increase, the angular deviation of the chief rays by the IOL increases as well. This is because the rays passing through the IOL go to the same focal point. Increasing angular deviation is shown in FIG. 5 between chief ray angles 50 and 65 degrees where the rays hit the optic. Then, at about 65 degrees, the angular deviation suddenly drops to zero as shown in FIG. 5. A discontinuous reduction in optical power is therefore shown in FIG. 5. In contrast, FIG. 7 illustrates gradual reduction in optical power. Increasing angular deviation stops at about 55 degrees, which corresponds to a higher angle outside of the eye. Then, the angular deviation decreases gradually (e.g., not suddenly as shown in FIG. 5). Thus, the optic, and particularly the attenuation optical zone 220, is configured to eliminate discontinuity in angular deviation of chief rays passing through the optic 200. A gradual reduction in optical power is therefore shown in FIG. 7.

As described herein, the attenuation optical zone 220 increases the size of the optical zone of the IOL. For example, in some implementations, the central optical zone 225 has a diameter of about 5-6 mm). The attenuation optical zone 220 can increase the diameter of the optic 200 by between about 0.5 mm and about 3 mm, for example, to achieve an optical diameter of between about 6 mm and about 8 mm. For example, the diameter of the optic can optionally be 6.0, 6.5 mm, 7, mm, 7.5 mm, or 8 mm. Exceeding 8 mm diameters adds a lot of volume and may create problems with fit. The larger optical zone size increases the ratio of the optical zone to the anterior capsulorhexis, which facilitates firmly attaching the remaining anterior part of the capsule to the anterior side of the IOL. This results in increasing the pressure on the posterior capsular bend, which lowers the risk of PCO. In conventional IOLs, the size of the optical zone is limited by the need to keep the optic volume low, which is an untenable goal with a full power IOL, e.g., at 8 mm diameter. In the IOLs with enlarged optical zone size as described herein, the full optical zone does not need to provide the full power, since the outer or peripheral optical portions of the IOL (e.g., the attenuation optical zone 220 shown in FIGS. 2A and 2C) only see light passing for extreme pupil sizes or extreme angles of incidence (e.g., 60-80 degrees, well outside the subject's functional peripheral vision). Therefore, the optical power of the IOL can be gradually reduced in the attenuation zone, which results in lower optic volume. In some implementations, optical power can be reduced down to zero Diopter (D) at the edge of the optical zone. Using this configuration, improved PCO protection can be achieved without the need for excessive volume. As shown in FIG. 2A, optical power is gradually reduced in the attenuation optical zone 220, e.g., the radii between about 2.5 mm and 4 mm.

Referring now to FIG. 3, a 3-D illustration of an example IOL is shown. The IOL has both an enlarged optical zone (e.g., including central and attenuation optical zones as shown in FIGS. 2A and 2C) and an increased vault height (e.g., as shown in FIGS. 2A and 2C). As described herein, either one of these IOL configurations can increase pressure at the posterior capsular bend, which can reduce the rate of PCO. As shown in FIG. 3, the IOL includes an optic 300 including an anterior surface 302 defining an anterior side of the optic 300 and a posterior surface 304 defining a posterior side of the optic 300. The posterior surface 304 opposes the anterior surface 302. The IOL shown in FIG. 3 has a negative shape factor. More negative shape factor, meaning more posterior, means higher vault height. The optic 300 also includes a haptic 350 attached to the optic 300. Haptics are configured to generally center the optic 300 within the capsular bag (e.g., capsular bag 20 shown in FIGS. 1A-1B) and/or transfer ocular forces to the optic 300. The use of haptics with IOLs are well known in the art. This disclosure contemplates using haptic configurations known in the art with IOLs described herein. Further, the optic 300 includes an edge 310 arranged between the anterior and posterior surfaces 302, 304. The edge 310 is cut parallel to the optical axis of the ophthalmic lens. In other words, the edge 310 and the posterior surface 304 form an angle of about 90 degrees. As described herein, the angle formed by the edge 310 and the posterior surface 304 can be between 45 degrees and 90 degrees.

Figure 4:
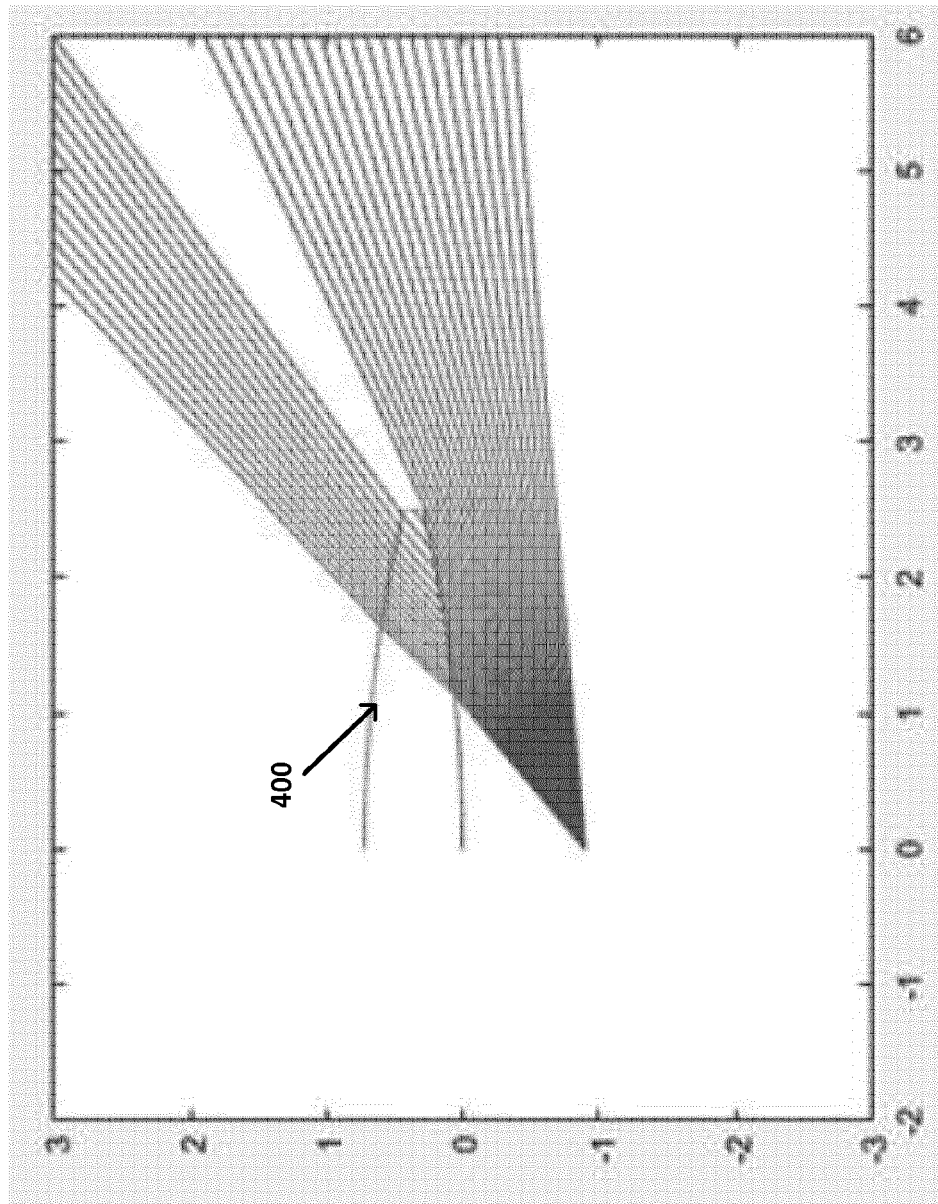
FIG. 4 is a diagram illustrating the chief ray passing through the center of a pupil at an angle between 50 and 85 degrees, for a biconvex IOL.
Figure 5:
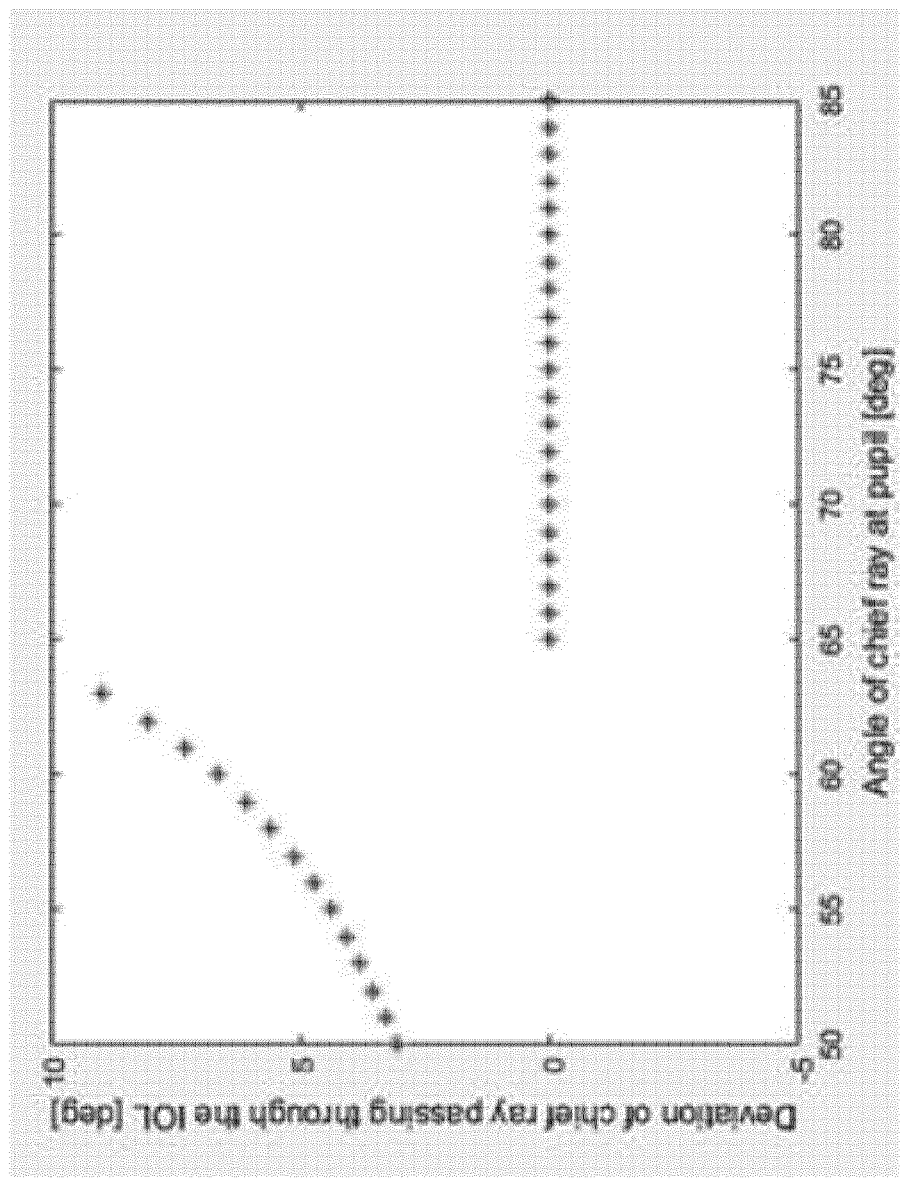
FIG. 5 is a diagram illustrating chief ray deviation as a function of angle for the biconvex IOL of FIG. 4.

Referring now to FIG. 4, a diagram illustrating the chief ray passing through the center of a pupil at an angle between 50 and 85 degrees, for a conventional biconvex IOL 400 is described. FIG. 4 is useful for understanding the cause of ND. FIG. 4 illustrates the path of the chief rays passing through the center of the pupil at angles between 50 and 85 degrees. The chief rays are either refracted by the biconvex IOL 400 or miss the biconvex IOL 400. Rays hitting the edge of the biconvex IOL 400 are assumed to be scattered/blocked, as the edge is often frosted. From FIG. 4, it is clear that there is an angular interval that will be perceived as a shadow. The behavior of the chief ray can be quantified as shown in FIG. 5, which illustrates chief ray deviation as a function of angle for the biconvex IOL of FIG. 4. As shown in FIG. 5, the discontinuity arises between about 63 degrees, where the deviation is 9 degrees, and about 65 degrees, where the chief ray pass the IOL creating a shadow of about 11 degrees in the extreme case, with partial illumination of the shadow area at larger pupil sizes.

In order to remove such discontinuity, an attenuation zone (e.g., the attenuation optical zone 220 shown in FIGS. 2A and 2C) for both the anterior and posterior sides of the IOL can be provided outside (e.g., disposed about, radially outward with respect to, etc.) the central optical part (e.g., the central optical zone 225 shown in FIGS. 2A and 2C). As described herein, such an IOL configuration can include the following design features. The beginning of the attenuation zone can be smooth and continuous, meaning that the height and the slope in the beginning of the attenuation zone is the same as the height and the slope in the end of the central optical part. In other words, the transition between the zones is smooth and continuous. Alternatively or additionally, the end of the attenuation zone can introduce minimal ray deviations as compared to a chief ray missing the IOL. Additionally, the end of the attenuation zone can have a predetermined position, thickness and slope.

This disclosure contemplates that the attenuation zone (e.g., size, dimensions, etc.) itself can be evaluated or optimized in order to fulfill the criteria above while minimizing ray deviations and slope variability within the zone. For example, a number of attenuation zone design parameters are discussed above. These design parameters include, but are not limited to, the size of the attenuation zone and/or edge thickness. For example, the attenuation zone can increase the total diameter of the optic (e.g., optic 200 shown in FIGS. 2A-2C) by between about 0.5 mm and about 3 mm, bringing the total IOL diameter to between about 6 mm to about 8 mm. Additionally, the edge thickness can, for example, be 0.1 mm, 0.2 mm, 0.3 mm, 0.4 mm or 0.5 mm. It should be understood that algorithms can be used to design, and in some implementations optimize, the attenuation zone of the IOL. For example, different designs with these functions can be evaluated (and optionally optimized) looking at a range of merit functions that include slope characteristics, variability, and magnitude of deviation between neighboring chief ray angles. Example algorithms can include, but are not limited to, analytical solutions fitting a third order polynomial, higher order aspheric functions, or splines. Such algorithms are known in the art and are therefore not described in further detail below. Additionally, the specific algorithms discussed above are provided only as examples. This disclosure contemplates that algorithms other than those discussed above can be used to evaluate or optimize the design.

One example design technique for the optic (e.g., optic 200 in FIGS. 2A-2C or optic 300 in FIG. 3) is now described. As described herein, the optic can include both central and attenuation optical zones (e.g., central optical zone 225 in FIGS. 2A and 2C and attenuation optical zone 220 in FIGS. 2A and 2C), and the transition between the central and attenuation optical zones is smooth an continuous. For optic design, symmetry is assumed to be circular and coordinates are used. One coordinate is the radial coordinate (e.g., zero (0) at the vertex of the optic). The other coordinate is the height, which is the difference between the vertex position and the surface height at any point on the optic other than the vertex. For spherical designs, the height as a function of radius can be described as a spherical function. The coefficients determine the optical quality. Design of IOLs using such a spherical function is known in the art and is therefore not described in further detail below.

For aspherical design, the height as a function of radius can be described as a spherical function with additional aspherical coordinates. It is not possible to construct an attenuation optical zone as described herein (e.g., attenuation optical zone 220 in FIGS. 2A and 2C) using a spherical function with additional aspherical coordinates using existing techniques. Instead, splines can be used to design the attenuation optical zone. A spline is a function defined by piecewise polynomials. Splines and spline interpolation are known in the art and are therefore not described in further detail below.

The attenuation optical zone can be designed by construction of splines according to a set of conditions. The conditions for the splines include establishing a first point and a second point. The first point can be the starting point for the attenuation optical zone. The thickness and slope at the starting point are continuous with the central optical zone (e.g., central optical zone 225 in FIGS. 2A and 2C). The second point can be the ending point for the attenuation optical zone at the edge of the optic, which is the farthest point radially outward from the center of the optic. The thickness and slope at the ending point are those at the edge of the optic (e.g., edge 210 in FIGS. 2A and 2B and edge 310 in FIG. 3). In some implementations, the slope (e.g., angle at the edge) is about 90 degrees. In other implementations, the slope (e.g., angle at the edge) is less than 90 degrees. The splines can be optimized in the region between the first and second points (e.g., the attenuation optical zone) by analyzing a merit function such as the slope deviation. This disclosure contemplates that splines can be optimized to give minimal total slope deviation. This results in an IOL having gradual decline in chief ray angular deviation as shown, for example, by FIGS. 7 and 9. In other words, there will be no discontinuity in chief ray angular deviation as shown in FIG. 5.

Figure 6:
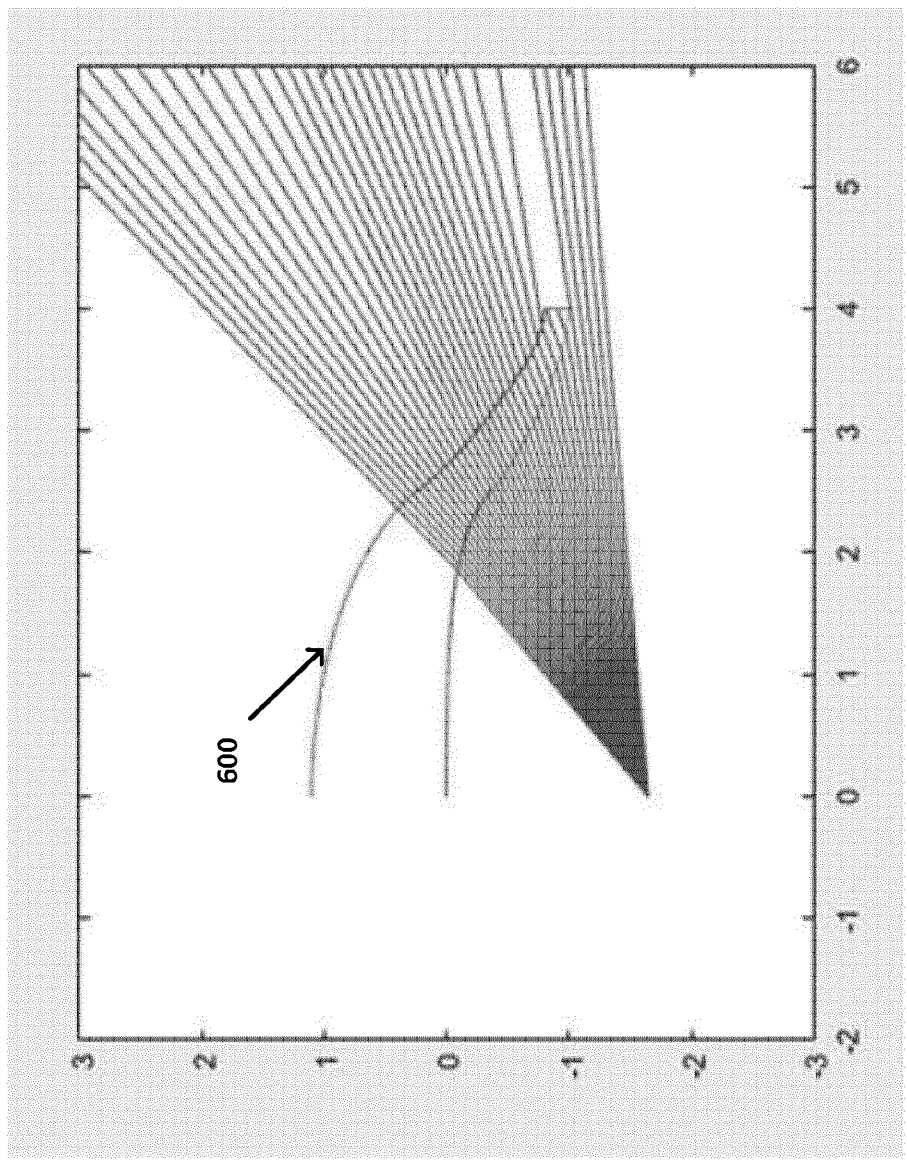
FIG. 6 is a diagram illustrating the chief ray passing through the center of a pupil at an angle between 50 and 85 degrees, for an IOL with an attenuation optical zone according to implementations described herein.
Figure 7:
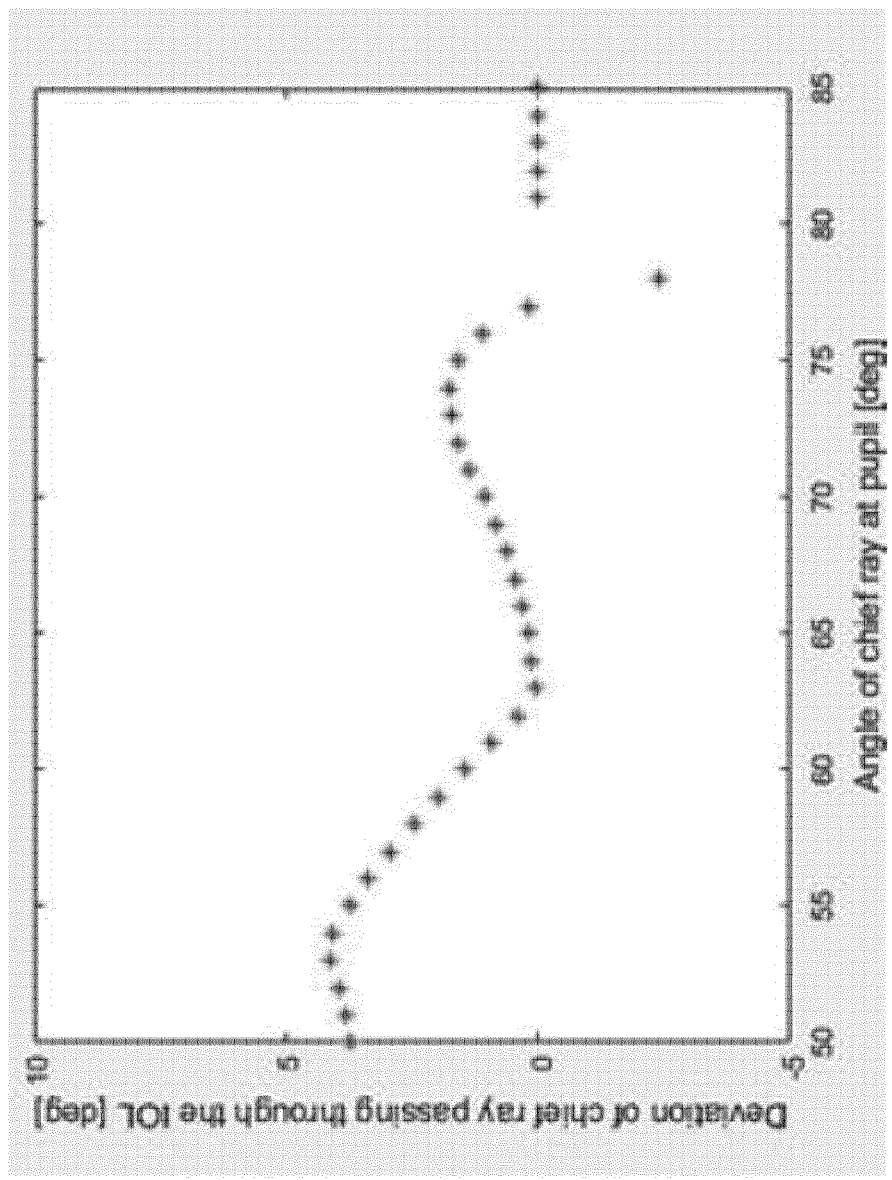
FIG. 7 is a diagram illustrating chief ray deviation as a function of angle for the IOL of FIG. 6.

Referring now to FIG. 6, a diagram illustrating the chief ray passing through the center of a pupil at an angle between 50 and 85 degrees, for an IOL 600 with an attenuation optical zone (e.g., the attenuation optical zone 220 shown in FIGS. 2A and 2C) is described. In FIG. 6, the IOL design is optimized for a high image quality in central and functional peripheral vision (e.g., up to 40 degrees) and includes the increased vault height, changed shape factor, and aspheric parts described in earlier patent applications, including U.S. patent application Ser. No. 15/456,356, filed on Mar. 10, 2017 and incorporated herein by reference. As shown in FIG. 6, the attenuation zone ensures minimal deviation between chief rays passing through the IOL 600 and missing the IOL 600, where the only shadow is due to the edge of the IOL 600. This smaller shadow is likely obscured by aberrated rays at realistic pupil sizes (e.g., 2 mm, 2.5 mm, or 3 mm). The behavior of the chief ray can be quantified as shown in FIG. 7, which illustrates chief ray deviation as a function of angle for the IOL of FIG. 6. As shown in FIG. 7, the discontinuity is reduced to 3 degrees and occurs at a significantly higher angle. In FIG. 7, the discontinuity occurs at about 80 degrees inside the eye, as compared to at about 65 degrees for the biconvex IOL as described with regard to FIGS. 4 and 5, where retinal sampling is lower.

Figure 8:
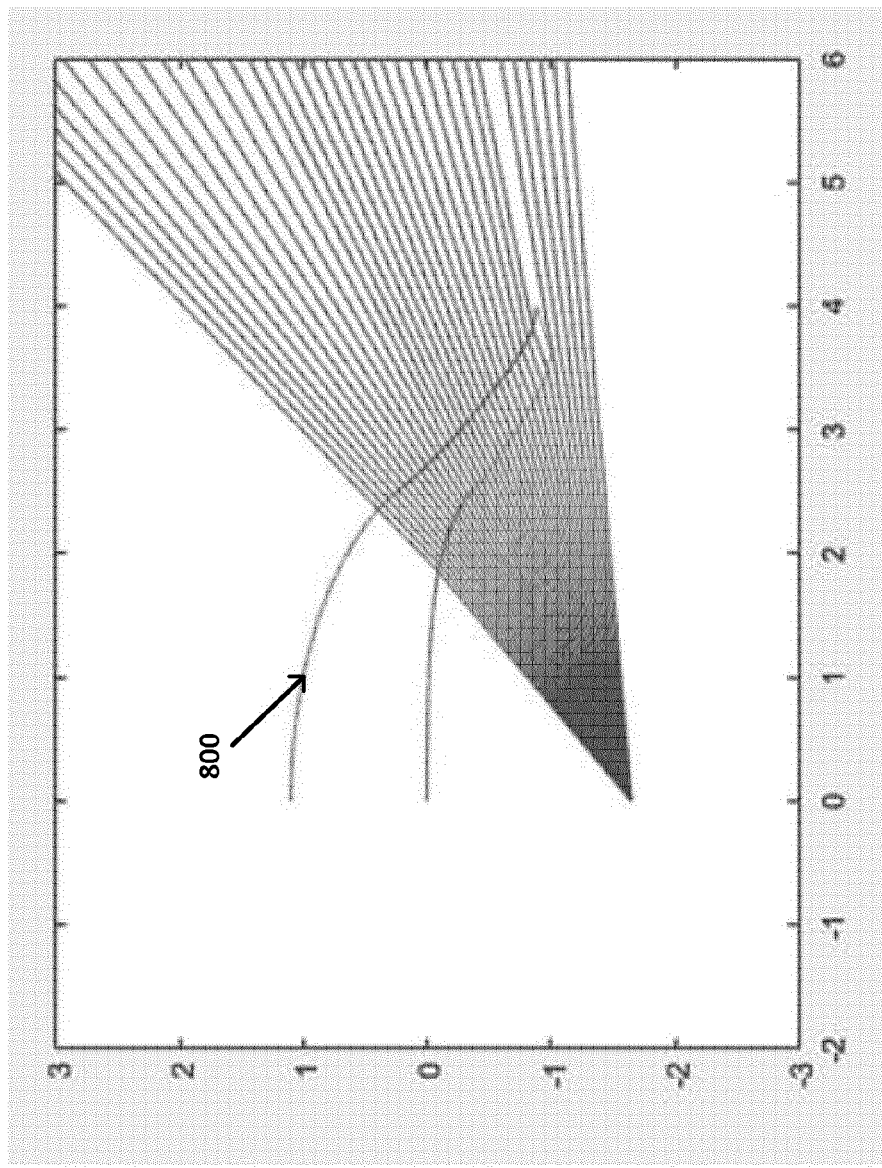
FIG. 8 a diagram illustrating the chief ray passing through the center of a pupil at an angle between 50 and 85 degrees, for an IOL with an attenuation optical zone and sharp edge design according to implementations described herein.
Figure 9:
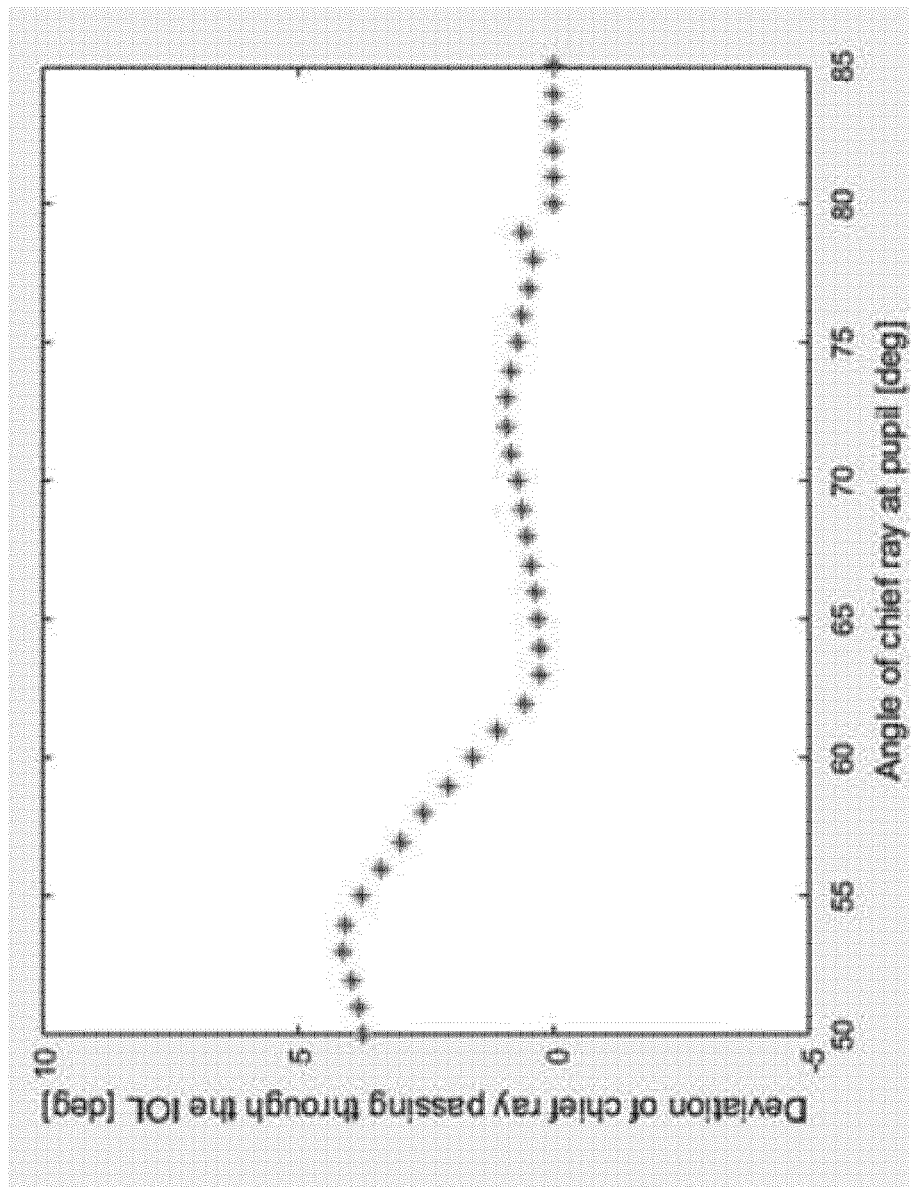
FIG. 9 is a diagram illustrating chief ray deviation as a function of angle for the IOL of FIG. 8.

The reduction of ND can further be enhanced by the introduction of an edge design (e.g., the sharper edge design such as edge 210 shown in FIGS. 2A and 2B or edge 310 shown in FIG. 3). As described above, in some implementations, the anterior side of the optic can have a smaller diameter than the posterior side of the optic, creating a sharp posterior edge rather than a 90-degree posterior edge. In other implementations, the anterior side of the optic can have the same diameter as the posterior side of the optic, creating a sharp posterior edge of about 90 degrees. Referring now to FIG. 8, a diagram illustrating the chief ray passing through the center of a pupil at an angle between 50 and 85 degrees, for an IOL 800 with both an attenuation optical zone (e.g., the attenuation optical zone 220 shown in FIGS. 2A and 2C) and a sharper edge design (e.g., the edge 210 shown in FIGS. 2A and 2B) is described. As shown in FIG. 8, this reduces the fraction of chief rays that will hit the edge of the IOL 800. The behavior of the chief ray can be quantified as shown in FIG. 9, which illustrates chief ray deviation as a function of angle for the IOL of FIG. 8.

The IOLs described herein can include an increased vault height as compared to conventional IOLs. For example, including an attenuation zone (e.g., the attenuation optical zone 220 shown in FIGS. 2A and 2C) can increase a vault height of the ophthalmic lens to between 0.35 mm and 1.5 mm. Having an increased vault height can create a higher pressure at the posterior edge and a faster wrapping of the capsule, which reduces the risk of PCO. The design shown in FIGS. 2A and 3 achieves that increased vault height primarily through placing most of the power on the posterior side, and having the enlarged optical zone size with gradually reduces power, which increases the vault height compared to a standard biconvex IOL with the same haptics. An optimal vault height depends on the combination of the following factors: power of the IOL, shape factor, edge thickness, and size of the attenuation optical zone. This disclosure contemplates increasing vault height up to about 1.5 mm.

Figure 10:
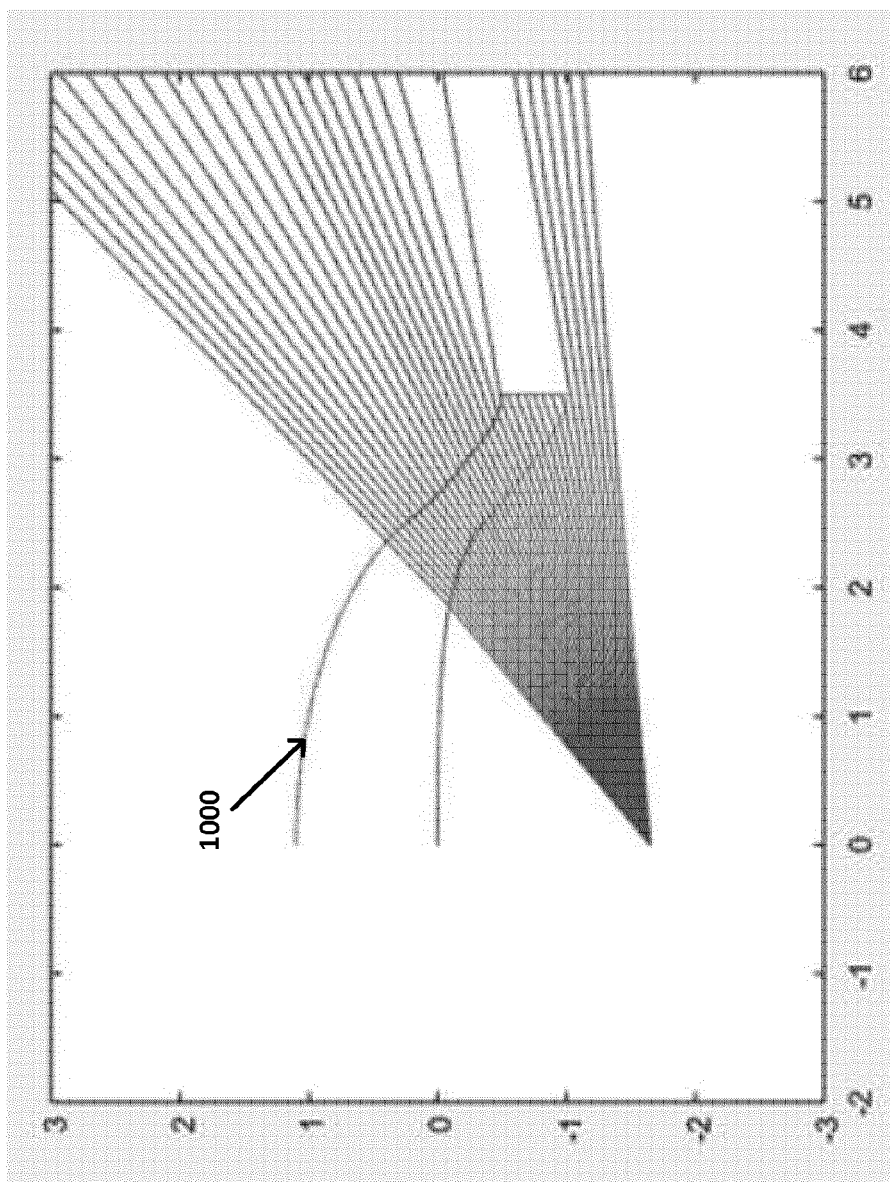
FIG. 10 is a diagram illustrating the chief ray passing through the center of a pupil at an angle between 50 and 85 degrees, for another IOL with an attenuation optical zone and sharp edge design according to implementations described herein.
Figure 11:
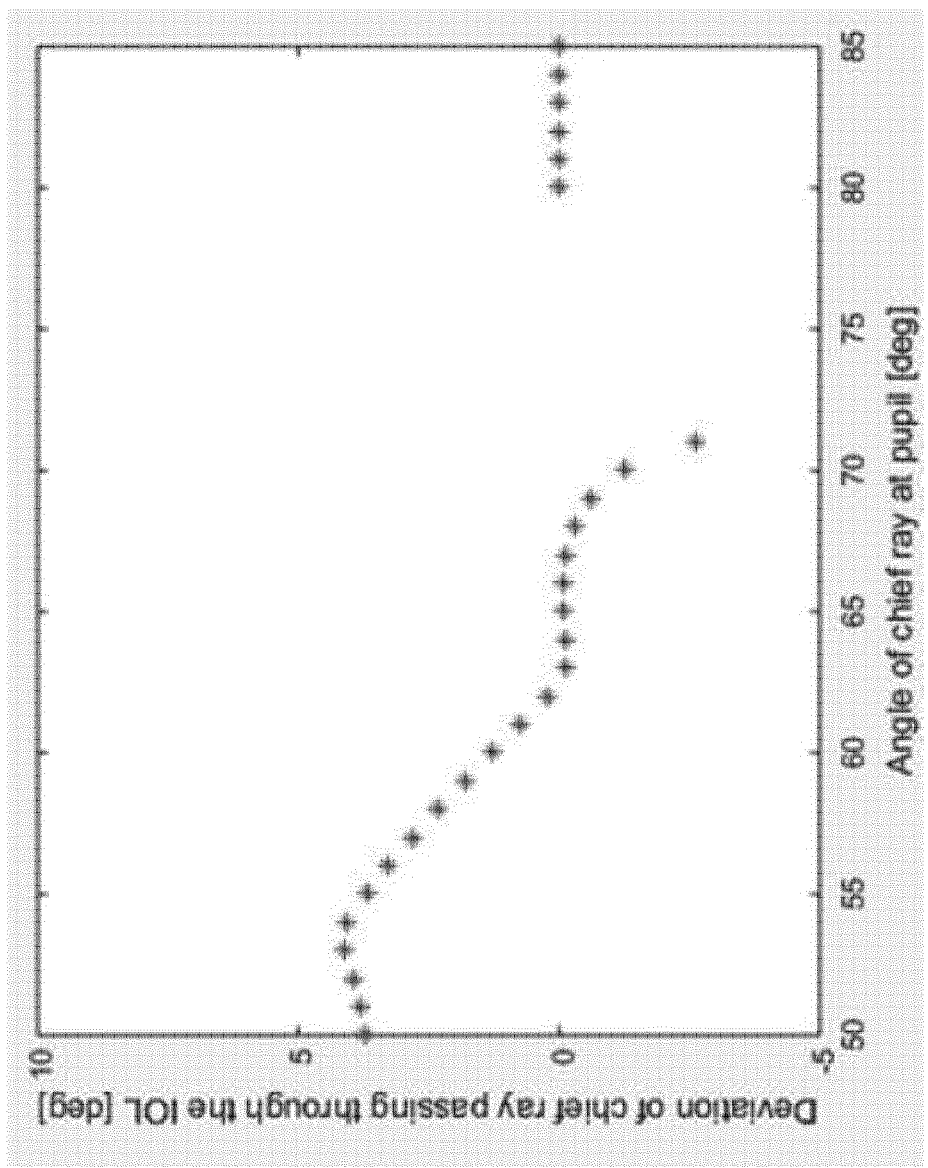
FIG. 11 is a diagram illustrating chief ray deviation as a function of angle for the IOL of FIG. 10.

Referring now to FIG. 10, a diagram illustrating the chief ray passing through the center of a pupil at an angle between 50 and 85 degrees, for an IOL 1000 with both an attenuation optical zone (e.g., the attenuation optical zone 220 shown in FIGS. 2A and 2C) and a sharp edge design with an angle of 90 degrees is described. The behavior of the chief ray can be quantified as shown in FIG. 11, which illustrates chief ray deviation as a function of angle for the IOL of FIG. 10. As shown in FIG. 11, at about 70 degrees of angle inside the eye, the chief ray hits the edge of the IOL, causing it to be scattered/blocked. At about 80 degrees angle inside the eye, the chief ray passes to the pupil. It should be understood that this discontinuity occurs for much higher angles than in existing commercial IOLs and that the last refracted angle at 70 degrees in FIG. 11 has a negative ray deviation (e.g., negative ray deviation means angle increases rather than decreases). This is advantageous since the last refracted rays at about 70 degrees partially fill the shadow. Therefore, in the visual experience, there will be no discontinuity.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. An ophthalmic lens, comprising:
an optic having a central optical axis and including:
an anterior surface defining an anterior side of the optic,
a posterior surface that opposes the anterior surface and that defines a posterior side of the optic,
a central optical zone disposed about the central optical axis,
an attenuation optical zone disposed about the central optical axis, wherein the attenuation optical zone is contiguous with the central optical zone, and wherein the central and attenuation optical zones define a negative shape factor for the optic,
an edge of the attenuation optical zone arranged between the anterior and posterior surfaces, wherein the edge of the attenuation optical zone and the posterior surface form an angle, wherein the angle is less than about 90 degrees, wherein the ophthalmic lens has a vault height between about 0.35 millimeter (mm) and about 1.5 mm, and wherein a combination of the angle and the vault height is configured to increase pressure on a capsular bend in a subject's eye.

2. The ophthalmic lens of claim 1, wherein the angle is between about 45 degrees and about 90 degrees.

3. The ophthalmic lens of claim 2, wherein the angle is less than about 85 degrees and greater than about 45 degrees.

4. The ophthalmic lens of claim 2, wherein the angle is less than about 80 degrees and greater than about 45 degrees.

5. The ophthalmic lens of claim 2, wherein the angle is less than about 70 degrees and greater than about 45 degrees.

6. The ophthalmic lens of claim 2, wherein the angle is less than about 60 degrees and greater than about 45 degrees.

7. The ophthalmic lens of claim 2, wherein the angle is less than about 50 degrees and greater than about 45 degrees.

8. The ophthalmic lens of claim 2, wherein a diameter of the anterior side of the optic is less than a diameter of the posterior side of the optic.

9. The ophthalmic lens of claim 1, wherein a diameter of the optic is between about 6 mm and about 8 mm.

10. The ophthalmic lens of claim 1, wherein the attenuation optical zone extends radially outward from the central optical zone, the edge of the attenuation optical zone being spaced apart from the central optical zone in an anterior direction along the optical axis.

11. The ophthalmic lens of claim 1, further comprising a haptic attached to the optic.

* * * * *